(12) United States Patent
Avniel et al.

(10) Patent No.: US 12,171,940 B2
(45) Date of Patent: *Dec. 24, 2024

(54) ENDOTRACHEAL TUBE INSERTION (71) Applicant: Aninimed LLC, Chicago, IL (US)

(72) Inventors: Yuval Avniel, Missoula, MT (US); Kai Matthes, Kula, HI (US)

(73) Assignee: Aninimed LLC, Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 18/342,124

(22) Filed: Jun. 27, 2023

(65) Prior Publication Data

US 2024/0207556 A1    Jun. 27, 2024

Related U.S. Application Data

(63) Continuation of application No. 16/522,581, filed on Jul. 25, 2019, now Pat. No. 11,684,737.

(60) Provisional application No. 62/703,457, filed on Jul. 26, 2018.

(51) Int. Cl.
*A61M 16/04* (2006.01)
*A61B 1/267* (2006.01)
*A61B 90/00* (2016.01)

(52) U.S. Cl.
CPC .... *A61M 16/0418* (2014.02); *A61M 16/0463* (2013.01); *A61M 16/0488* (2013.01); *A61M 16/049* (2014.02); *A61M 16/0497* (2013.01); *A61B 1/267* (2013.01); *A61B 2090/062* (2016.02); *A61B 2090/0807* (2016.02); *A61M 2205/583* (2013.01)

(58) Field of Classification Search
CPC .......................... A61M 16/0488; A61B 1/267
See application file for complete search history.

(56) References Cited

U.S. PATENT DOCUMENTS

| 3,968,800 | A | * | 7/1976 | Vilasi | A61M 16/0431 |
| | | | | | 128/207.14 |
| 4,141,364 | A | * | 2/1979 | Schultze | A61M 16/0434 |
| | | | | | 128/207.15 |
| 4,530,354 | A | * | 7/1985 | Froilan | A61M 25/02 |
| | | | | | 128/207.17 |

(Continued)

FOREIGN PATENT DOCUMENTS

| KR | 20100049796 A |   | 5/2010 |
| KR | 20100049769 A | * | 11/2010 |

(Continued)

OTHER PUBLICATIONS

United States Patent and Trademark Office, Non-Final Office Action, U.S. Appl. No. 16/522,592, dated Dec. 24, 2021, 12 pages.

(Continued)

*Primary Examiner* — Kathryn E Ditmer
(74) *Attorney, Agent, or Firm* — Sunstein LLP (57) ABSTRACT

An intubation system includes: a base configured to be secured relative to a subject; a guide movably coupled to the base to allow the guide to move relative to the base; and a connector configured to be connected to a distal end of the guide and to detachably connect to an endotracheal tube such that as the guide is moved relative to the base toward the subject, the endotracheal tube is inserted into the subject.

16 Claims, 7 Drawing Sheets

(56) References Cited

U.S. PATENT DOCUMENTS

| | | | | |
|---|---|---|---|---|
| 4,722,335 A | * | 2/1988 | Vilasi | A61M 16/04 128/207.14 |
| 4,727,872 A | * | 3/1988 | Hawk | A61M 25/02 128/207.14 |
| 4,827,925 A | * | 5/1989 | Vilasi | A61M 16/04 128/207.14 |
| 4,960,122 A | * | 10/1990 | Mizus | A61M 16/0488 128/207.14 |
| 5,163,941 A | * | 11/1992 | Garth | A61M 16/0461 24/518 |
| 5,178,132 A | * | 1/1993 | Mahefky | A61B 1/267 600/199 |
| 5,184,603 A | * | 2/1993 | Stone | A61B 1/2676 600/193 |
| 5,259,371 A | * | 11/1993 | Tonrey | A61M 16/04 128/207.14 |
| 5,647,358 A | * | 7/1997 | Vilasi | A61M 16/0418 128/207.14 |
| 5,791,338 A | * | 8/1998 | Merchant | A61M 16/0488 128/207.14 |
| 5,873,858 A | * | 2/1999 | Schafer | A61M 16/0488 128/207.14 |
| 5,951,461 A | * | 9/1999 | Nyo | A61B 1/00149 600/117 |
| 6,520,954 B2 | * | 2/2003 | Ouchi | A61B 10/0275 606/1 |
| 6,631,713 B1 | | 10/2003 | Christopher | |
| 6,668,821 B2 | | 12/2003 | Christopher | |
| 7,328,701 B2 | * | 2/2008 | Green | A61M 16/04 128/207.14 |
| 8,382,665 B1 | * | 2/2013 | Fam | A61B 1/00108 128/200.26 |
| 8,734,327 B2 | * | 5/2014 | Dillon | A61M 25/0113 600/102 |
| 8,813,750 B2 | * | 8/2014 | O'Neil | A61M 16/0427 128/207.14 |
| 2003/0024532 A1 | * | 2/2003 | Sniadach | A61B 13/00 128/205.13 |
| 2007/0191876 A1 | | 8/2007 | Dubrul et al. | |
| 2008/0115789 A1 | | 5/2008 | Green | |
| 2009/0050146 A1 | * | 2/2009 | Smith | A61M 16/0488 128/200.26 |
| 2009/0264708 A1 | * | 10/2009 | Pacey | A61B 1/00103 600/187 |
| 2010/0313896 A1 | | 12/2010 | O'Neil et al. | |
| 2011/0146689 A1 | * | 6/2011 | Curley | A61M 16/04 128/207.14 |
| 2011/0180072 A1 | * | 7/2011 | Morejon | A61M 16/0486 128/207.14 |
| 2011/0263935 A1 | * | 10/2011 | Qiu | G06F 18/2415 382/128 |
| 2013/0237763 A1 | * | 9/2013 | Qiu | A61M 16/0488 600/188 |
| 2017/0333147 A1 | * | 11/2017 | Bernstein | A61B 34/30 |
| 2021/0228289 A1 | * | 7/2021 | Rohr Daniel | B25J 9/10 |

FOREIGN PATENT DOCUMENTS

| | | | | |
|---|---|---|---|---|
| WO | WO-2011139620 A2 | * | 11/2011 | A61M 16/04 |
| WO | WO-2015110774 A1 | * | 7/2015 | A61M 16/0427 |
| WO | WO-2018082980 A1 | * | 5/2018 | A61M 16/0418 |

OTHER PUBLICATIONS

United States Patent and Trademark Office, Final Office Action, U.S. Appl. No. 16/522,592, dated Aug. 18, 2022, 13 pages.
United States Patent and Trademark Office, Non-Final Office Action, U.S. Appl. No. 16/522,592, dated Dec. 8, 2022, 14 pages.

* cited by examiner

ENDOTRACHEAL TUBE INSERTION

CROSS-REFERENCE TO RELATED APPLICATIONS

This application claims priority to U.S. application Ser. No. 16/522,581, filed Jul. 25, 2019, entitled, "ENDOTRACHEAL TUBE EXCHANGE," which claims the benefit of U.S. Provisional Application No. 62/703,457, filed Jul. 26, 2018, entitled "ENDOTRACHEAL TUBE EXCHANGE," both of which are assigned to the assignee hereof, and the contents of both of which are hereby incorporated herein by reference in their entireties.

BACKGROUND

While critically ill patients experience a life-threatening illness, they are also at risk from secondary conditions such as nosocomial infection. Pneumonia is the second most common nosocomial infection in critically ill patients, affecting approximately 27% of all critically ill patients. Eighty-six percent (86%) of nosocomial pneumonias are associated with intubated patients, i.e., those that experience mechanical ventilation. Pneumonia that results due to intubation is commonly termed ventilator-associated pneumonia (VAP). In the United States alone, more than 300,000 cases of VAP occur per year, which is an incidence rate of between 5 to 10 cases per 1,000 hospital admissions. The mortality rate attributable to VAP has been reported to range up to 50% of those infected. Beyond mortality, the economics of VAP include increased ICU lengths of stays, which on average range from 4 to 13 days. Further the incremental costs associated with VAP have been estimated at between $5,000 and $20,000 per diagnosis.

For those patients requiring controlled ventilation, an endotracheal tube (ETT) is typically employed for insertion in a patient through the mouth for the purpose of ventilating the lungs. Insertion of an ETT may be through the mouth, the nasal passage, or direct access to the trachea via tracheostomy. The tube passes through the normally restricted glottis or passageway between the vocal chords and may terminate adjacent or near adjacent the entrance to the bifurcation of trachea into the right and left main stem bronchus. Using an ETT that seals well to the trachea helps ensure oxygen is delivered to the patient's lungs and helps prevent loss of oxygen or air by leakage of gases to the exterior instead of going to the ventilated lungs.

To accommodate patients having differently sized tracheas, a variety of endotracheal tubes of different diameters may be available to permit selection of the proper size tube for the patient. ETT may differ in size in length and/or diameter. ETTs with small cross-sectional diameters can result in insufficient or turbulent airflow delivery to the patient. Conversely, an ETT with too large a tube diameter may be difficult to pass the ETT through the vocal cords into the trachea, often resulting in trauma and/or complications for the patient, and may increase the time it takes to intubate the patient. Further, an ETT that is too large may also cause pressure on the trachea, which can result in tracheal inflammation, necrosis and consecutive stenosis.

Patients requiring prolonged mechanical ventilation usually require replacement of an ETT to prevent biofilm formation which puts patients at risk for ventilator-associated pneumonia (VAP). The replacement of an ETT, referred to as ETT exchange, may be performed by withdrawing the tube from the trachea and inserting a new tube into the trachea. This procedure is complicated, time consuming and incurs a high degree of risk to the patient. Further, re-intubation often requires a skilled hand to position a new ETT in the trachea properly. An ETT should be exchanged (i.e. replaced with a fresh ETT) after 2-3 days of use to reduce risk of VAP, with this exchange being termed re-intubation. Re-intubation involves removal of the ETT and placement of a new ETT under direct vision using a standard laryngoscope or video laryngoscope. Re-intubation is considered more challenging than the first intubation since the presence of the ETT in the patient over a series of days typically causes tissue swelling. This tissue swelling may impede visualization of the vocal cords during re-intubation attempts.

SUMMARY

An example of an intubation system includes: a base configured to be movably connected relative to a subject; a guide movably coupled to the base to allow the guide to move relative to the base; and a connector configured to be connected to a distal end of the guide and to detachably connect to an endotracheal tube such that as the guide is moved relative to the base toward the subject, the endotracheal tube is inserted into the subject.

Implementations of such a system may include one or more of the following features. The guide includes a rod and a guide lock mechanism configured to lock the rod in place relative to the base. The guide includes a depth gauge. The depth gauge is indicative of a position of the endotracheal tube relative to the base. The guide includes a depth lock mechanism configured to inhibit movement of the guide past a location corresponding to the depth lock mechanism to inhibit insertion of the endotracheal tube beyond a threshold depth in the subject. The base includes a mouthpiece having a shape approximating a shape of a face of the subject adjacent a mouth of the subject. The system includes the endotracheal tube, and the endotracheal tube is an expandable endotracheal tube configured such that at least a portion of a length of the endotracheal tube has an expandable cross-section.

Another example of a intubation system includes: means for guiding an endotracheal tube into an existing endotracheal device in a subject; means for holding the endotracheal tube in place relative to the subject while the existing endotracheal device is extracted from the subject; and means for releasing the endotracheal tube.

Implementations of such a system may include one or more of the following features. The system includes means for indicating a depth of the endotracheal tube in the subject. The system includes means for inhibiting insertion of the endotracheal tube beyond a desired depth in the subject. The means for guiding include means for movably connecting the means for guiding relative to the subject.

An example method of intubating a subject includes: movably connecting a guide mechanism relative to the subject; attaching the guide mechanism to an endotracheal tube; inserting the endotracheal tube into an existing endotracheal device disposed in the subject until a desired insertion depth is reached as indicated by the guide mechanism; and extracting the existing endotracheal device from the subject.

Implementations of such a method may include one or more of the following features. The method includes setting the desired insertion depth on the guide mechanism before inserting the endotracheal tube into the subject. The method includes detaching the guide mechanism from the endotracheal tube after extracting the existing endotracheal device from the subject. The method includes expanding a cross-sectional area of the endotracheal tube to seal the endotracheal tube against a wall of a trachea of the subject after extracting the existing endotracheal device from the subject. Attaching the guide mechanism to the endotracheal tube includes attaching the guide mechanism to the endotracheal tube at a connection point of the endotracheal tube such that the connection point is fixed relative to a length of the guide mechanism.

DETAILED DESCRIPTION

Techniques are provided for intubating, including re-intubating, a patient, e.g., for placing or exchanging a device (e.g., an endotracheal tube (ETT)) adapted to be inserted and exchanged in a body opening for carrying out therapeutic and/or other medical procedures. For example, an ETT securement apparatus is fixed about an intubated patient. The securement apparatus may provide a stable platform that facilitates insertion of an ETT, such as an expandable ETT, within an inner diameter of an existing endotracheal device, e.g., an existing ETT or other device (e.g., a conduit) that is already present within a patient's trachea. The securement apparatus secures the ETT in a static position within the patient's existing endotracheal device while maintaining access to the airway passage of the patient. This continued control of access to the trachea during the insertion (e.g., exchange) may provide enhanced safety of ETT insertion with a lower risk of losing the airway and less trauma during ETT insertion. The ETT is inserted into the lumen of the already-present endotracheal device. The ETT is protected and guided during the placement by the already-present endotracheal device by having the ETT positioned inside the lumen of the already-present endotracheal device. This procedure of ETT insertion may be more controlled with less risk of airway damage or trauma. The discussion herein focuses on re-intubating a subject by replacement of an ETT by inserting a replacement ETT into an existing (used) ETT, but the discussion applies to initial insertion of an ETT into a subject by inserting an ETT into an existing endotracheal device other than an ETT such as an expandable endotracheal conduit, e.g., as discussed in U.S. Ser. No. 16/522,592, entitled "EXPANDABLE ENDOTRACHEAL DEVICE," filed Jul. 25, 2019.

The replacement ETT is inserted until an indicator (e.g., a positioning mark and/or insertion depth gauge) on the ETT and/or on the securement apparatus indicates that a specific ETT insertion depth beyond which further insertion is not desirable (or possibly not possible) has been reached (e.g., the positioning mark becomes aligned with a defined position). The indicator may be age and patient size dependent and is configured before insertion of the replacement ETT. The replacement ETT comprises an endotracheal tube that may be capable of being expanded transversely across a cross section of the ETT, that has an air passageway therein, and that may include a detachable connector positioned at a proximal end of the replacement ETT. The detachable connector is configured to be connected to a ventilator. The existing ETT is removed by sliding the existing ETT over the replacement ETT until the existing ETT clears the detachable connector and is removed out of the mouth of the patient being intubated. The replacement ETT is disconnected from the securement apparatus and expanded across a cross-sectional area of the replacement ETT such that the replacement ETT seals the patient's trachea in a manner compatible with mechanical ventilation. The securement apparatus and the existing ETT are removed from their positions about the patient. A ventilator connector is connected to the detachable connector of the replacement ETT, and the ventilator connector is connected to a circuit that is connected to a ventilator to enable ventilation of the patient.

Also discussed herein are adjustable-cross-sectional-area endotracheal tubes that may assume a relatively small outer perimeter for insertion into an existing endotracheal tube and upon actuation expand their cross-sectional areas at the discretion of a user. Such a tube may thus sufficiently seal an interface between the adjustable-cross-sectional-area endotracheal tube and the trachea in which the tube is disposed while an inner passageway is of a size, post expansion, that is amenable to adequate flow of intubation gases.

Items and/or techniques described herein may provide one or more of the following capabilities, as well as other capabilities not mentioned. A patient may undergo endotracheal tube insertion (e.g., exchange) with lower risk of bleeding, trauma, airway perforation, or needless exposure to subsequent intubation attempts, than with previous techniques. A patient may undergo ETT insertion with lower risk of inadequate ventilation than with previous techniques. Risk of VAP due to delayed re-intubation of a patient may be reduced because physicians may elect to exchange the ETT earlier due to the lower risk of the procedure. Time used for ETT exchange in a patient may be reduced compared to prior techniques. ETT insertion in a patient may be performed by a person other than a doctor, e.g., a nurse. A direct exchange of an ETT that does not require laryngoscopy would likely be associated with less risk and could potentially be performed by personnel not trained in endotracheal intubation. An ETT may be placed, or replaced, with correct placement, in a timely manner with a reduced risk of complications. ETT insertion may be performed in an efficient, safe and repeatable manner. ETTs may be exchanged without losing control of airway access and function. An ETT may be inserted into a patient to a predefined depth of insertion. ETTs may be inserted by a person without a high degree of training. An ETT exchange system may provide continued control of a trachea and uninterrupted ability to ventilate lungs while ETTs are exchanged. An ETT insertion system may help avoid trauma to soft tissue, vocal cords, and/or arytenoid cartilage while an ETTs is inserted. An ETT exchange system may allow replacement of one ETT with another ETT with the ability to deliver medications to treat and/or prevent VAP. Other capabilities may be provided and not every implementation according to the disclosure must provide any, let alone all, of the capabilities discussed.

Endotracheal intubation typically includes the act of introducing an ETT, into a patient's trachea to provide a controlled airway, prevent aspiration (gastric contents getting into the lungs) and provide positive pressure ventilation. Airway control is essential for life in the unconscious patient or the patient who is unable to protect the patient's airway. Endotracheal intubation allows ventilation of an unconscious patient, reduces aspiration risk, enables introduction of medicinal gases during surgery, presents an alternative drug route, and allows foreign body visualization and removal. Re-intubation typically involves removing one ETT and inserting a new one, essentially from scratch except that inserting the new ETT may be more complicated due to the previous intubation. An airway exchange catheter (AEC) may be used to exchange an ETT. The AEC slides over the existing ETT to allow removal (extubation) of the ETT, but this is undesirable, e.g., as the ETT may catch on the vocal cords as attempts are made to pass it blindly via the AEC into the trachea. This may be associated with complications such as damage to the vocal cords, arytenoids, soft tissue or pneumothorax.

While the discussion herein focuses on insertion of endotracheal tubes via the mouth, the methodologies described can be applied to other orifices. Further, while the discussion herein may refer to diameters of tubes, tubes as discussed herein may not be circular in cross-section, may not have circular inner surface cross-sections, and/or may not have circular outer surface cross-sections. For example, tubes may have oval perimeters and/or rectangular inner surfaces, or may have other shapes of outer surfaces and/or inner surfaces. Thus, reference to a diameter for an area or perimeter is an example and the description may apply to non-circular shapes. The term "patient" is used herein, but this does not imply that the discussion is limited to humans. The discussion herein may be applicable to use with a variety of subjects including humans, non-human animals, etc., and thus a "patient" could be any of such subjects.

Figure 1:
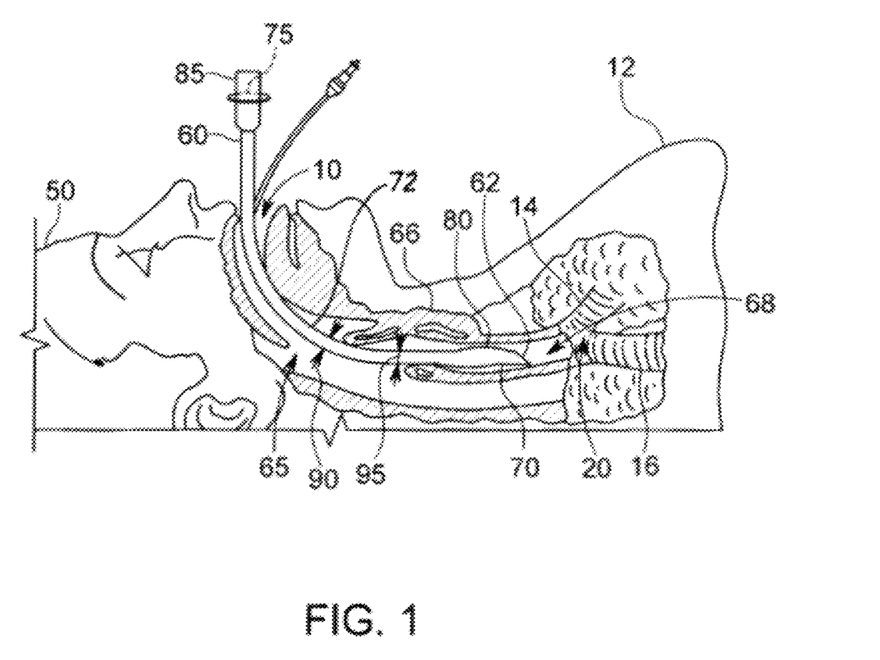
FIG. 1 is a partially-cross-sectional side plan view of a mouth and throat of an intubated patient.

Referring to FIG. 1, an ETT 60 is positioned in an airway 10 of a patient 12 passing through an oropharynx 65, by vocal cords 66, and with a tip 62 of the ETT 60 disposed in a trachea 68 above a bifurcation 20 of the trachea 68 into a right mainstem bronchus 16 and a left mainstem bronchus 14. The ETT 60 has a distal end 70 and a proximal end 75. The distal end 70 has a balloon cuff 80 inflated within the trachea 68. The proximal end 75 has a ventilator attachment 85. The ETT 60 may also include any suitable number of lumens (not shown) that may be appropriately sized and shaped for intubation or other intubation-associated procedures which may include selective ventilation of the right or left mainstem bronchus for surgery of the lungs. The ETT 60 has an outer diameter 90 and an inner diameter 95, although the ETT 60 could have a non-circular cross-section in other embodiments. The ETT 60 is, in this example, an expandable ETT (EETT) with the diameters 90, 95 being expandable such that the ETT 60 has a variable cross-sectional area size.

The use of EETTs may make intubation easier for a clinician and safer for the patient because the ETT may be passed more easily through the vocal cords due to the smaller diameter than a standard, non-adjustable ETT. This may benefit health care providers using the smaller diameter ETT for primary intubation as it may be easier to intubate the patient due to the lower profile. Further, EETTs may decrease patient discomfort during insertion as the relatively smaller cross-sectional diameters, as compared to a typical endotracheal tube, may irritate the patient's internal passageway less if at all. Further, upon expansion, the EETT may offer dynamic sealing between the ETT and the trachea 68, different pressures to different portions of the patient (e.g., less pressure to vocal cords or other sensitive areas (prior surgical sites) than areas of the trachea 68), as well as a large inner diameter to facilitate easy flow of respiratory gases. A larger inner diameter would favor more laminar gas flow with less resistance than a smaller inner diameter ETT.

The distal end 70 of the ETT 60 is configured for intubation into a patient, an intermediate portion 72 is configured to be expandable to adjust to the patient 12, and the proximal end 75 is configured for connection to other medical systems, such as a ventilator (not shown). The intermediate portion 72 is made of a structure and/or mechanism which is capable of expanding from an initial small cross-sectional diameter to a larger cross-sectional diameter at the discretion of a user. The distal end 70 may be shaped and sized as in typical endotracheal tubes. The distal end 70 may be made of any suitable material (e.g., medical-grade material) that is suitably rigid. For example, the distal end 70 may be polyvinyl chloride. The relative rigidity of the distal end 70 facilitates guiding the ETT 60 through the patient's larynx and trachea 68. As such, the distal end 70 may be softer than the intermediate portion 72 to facilitate guidance through the larynx and into the trachea 68 while causing less trauma to tissue. Suitable materials for the distal end 70 may also include silicone, rubber, or polyurethane. Other existing medical-grade materials may be used as well as medical-grade materials developed in the future. The description of materials is not limiting, but provides a non-exhaustive list of example materials capable of performing in an acceptable manner. The distal end 70 may be attached to the intermediate portion 72 by any suitable means, such as by adhesives or heat-sealing, solvent bonding, RF (radio frequency) sealing, or ultrasonic welding, or any other techniques of attachment. Alternatively, the ETT 60 may be extruded as a single tube and the intermediate portion 72 maybe blow-molded to have relatively thinner walls than the distal end 70 or the proximal end 75. As an example, the outer diameter of the distal end 70 may be between about 1 mm and about 14 mm. The outer diameter dimension used may depend on whether the patient 12 is a pediatric patient or an adult patient.

The distal end 70 may be any suitable length. For example, for use with humans, the distal end 70 may be between about 1 mm and about 14 mm although other lengths may be used, especially for non-human applications. In addition, the distal end 70 may include an opening in a side wall near a distal opening at a tip 62. This opening is often called a "Murphy eye" and may serve as an alternative path for gas in the event that the distal opening becomes blocked. Also, the tip 62 maybe beveled to allow for smoother insertion through the larynx and into the trachea 68. Further, the tip 62 may be made of a pliable material thereby lessening the instance of trauma produced by the distal end 70 upon insertion to the trachea 68.

As with the distal end 70, the proximal end 75 may be formed from conventional medical-grade plastics or polymers, including medical-grade polyvinyl chloride. The proximal end 75 may be attached to the intermediate portion 72 by any suitable means, such as by adhesives, heat sealing, being produced in a single action (e.g., extrusion) and/or other means as is known in the art. The proximal end 75 may be capable of being attached and detached from other medical systems, including a ventilator and/or a placement guide as discussed herein. As such, the proximal end 75 may terminate with a coupling, such as a quick-disconnect coupling (not shown) or a standard 15 mm outer diameter coupling. In a specific embodiment, the outer diameter of the proximal end 75 may be between approximately 1 mm and approximately 14 mm, with the size used possibly depending on whether the patient 12 is a pediatric patient or an adult patient. The proximal end 75 maybe any suitable length such as between about 0.1 cm to about 50 cm, or even longer.

Further, as the proximal end 75 may be manipulated by medical staff during insertion and connection of the ETT 60, the proximal end 75 may be somewhat rigid. Further, at least a portion of an outer diameter of the proximal end 75 may be between about 15 mm and about 16 mm. The diameter of the proximal end 75 may be configured to allow direct connection of the proximal end 75 to ventilator tubing directly with standard connection pieces to provide convenience and fitting options.

The intermediate portion 72 of the ETT 60 includes a structure capable of expanding in diameter. As depicted in FIG. 1, the intermediate portion 72 is in a partially expanded state. The intermediate portion 72 may contract such that the inner diameter 95 is relatively smaller than an inner diameter of the proximal end 75 or an inner diameter of the distal end 70. A maximum size of the outer diameter 90 of the intermediate portion 72 may be measured prior to insertion into the patient 12, as this value may be larger than a tracheal diameter. After insertion into the patient 12, an outer surface of the intermediate portion 72 may generally conform to the wall of the trachea 68, with the outer surface being constrained from further expansion by the trachea wall. The intermediate portion 72 may be pliable to help the outer surface of the intermediate portion 72 adapt and conform to the wall of the trachea 68. The ETT 60 may be configured to help ensure that pressure from the ETT 60 applied onto the wall of the trachea 68 will not exceed perfusion pressure of mucosal tissue, which could lead to necrosis. The ETT 60 may be configured to help ensure that pressures applied by the ETT 60 on anatomically-sensitive portions of a subject (e.g., vocal cords) do not cause permanent (or possibly even temporary) damage. Further, external pressure should not exceed the tissue perfusion pressure which would then result in ischema followed by necrosis. Generally speaking, such tissue perfusion pressure is usually within the range of 20-30 mm Hg but depends on mean arterial and venous pressure. The distal end 70 may also be configured to be expandable over at least a portion of a length of the distal end 70.

Figure 2A:
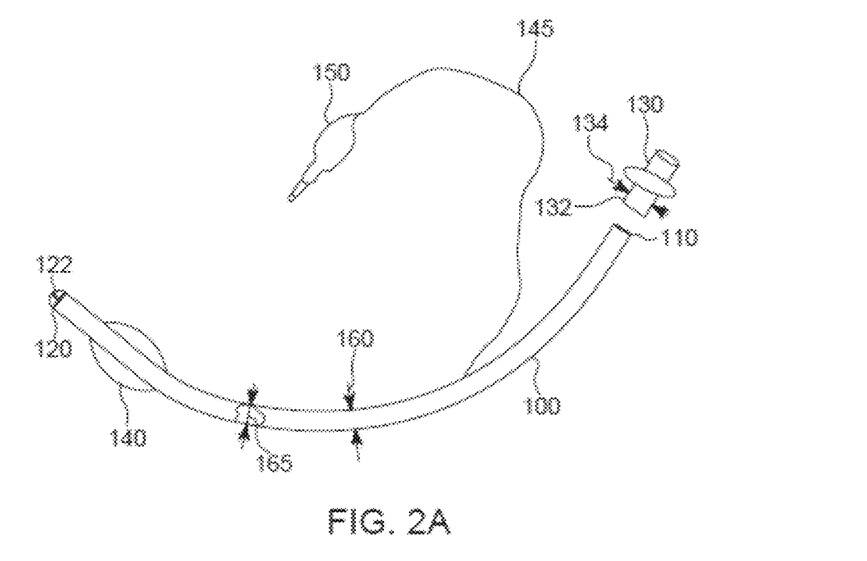
FIG. 2A is partially-cut-away side plan view a replacement ETT.

Referring also to FIG. 2A, a replacement ETT 100 includes a body 105 that has a proximal end 110 and a distal end 120. The proximal end 110 is capable of detachably receiving a detachable ventilator connector 130. The connector 130 is configured to be connected to a ventilator (not shown). The ETT 100 may include a cuff 140, sometimes referred to as a balloon cuff, near the distal end 120 and may include a pilot tube 145 and a pilot tube balloon 150 as is known in the art. The replacement ETT 100 is an EETT configured to have an expandable diameter 160. For example, the diameter 160 may have a range from a minimum diameter that is less than an inner diameter of an ETT that the ETT 100 will replace to a maximum diameter that is at least big enough to enable ventilation as is known in the art. The replacement ETT 100 also has an inner diameter 165 sized to receive air/oxygen for ventilation of the patient 12 during the ETT exchange procedure. The replacement ETT 100 may include a scale on or in the ETT 100 indicative of distances to a tip 122 of the ETT 100. The replacement ETT 100 may include one or more other features such as a soft nose, medically safe materials, sufficient structural stability to perform intubation, ability to interface with a ventilator, a Murphy eye, etc. Although called a replacement ETT, the replacement ETT 100 could be used for initial intubation, and thus not used as a replacement for another ETT. This technique serves as a type of bougie making the initial intubation less challenging due to the smaller diameter of the ETT.

Any of a variety of different expansion methodologies can be used to facilitate expansion and/or contraction of the diameter 160. For example, the ETT 100 may be configured similarly to self-expandable metallic stents. As other examples, the ETT may be configured with an expansion mechanism such as cross-hatched, braided, or interconnecting rows of material that are assembled into a tube-like structure that can be expanded. As other examples, shape memory alloys such as Nitinol (nickel titanium alloy) can be used in the construction of suitable expandable ETTs. As other examples, plastic self-expanding systems such as those based on self-expanding plastics, such as Polyflex™ made by Boston Scientific, may be used. Also or alternatively, a sleeve may be used that restricts expansion until the sleeve is removed from the device upon which the sleeve is placed. Upon removal of the sleeve, the device expands until restricted by an outside source (e.g., trachea wall) or is restricted by device design such that the device cannot expand beyond a certain diameter. The expansion may not be uniform, i.e., an expandable tube cross section may not always be circular, and thus while the discussion above focused on expandable diameters, the discussion applies to expandable cross-sectional areas of circular and non-circular perimeter shapes (e.g., a perimeter shape may adapt to a constraining shape such as a trachea wall, including variations and/or anomalies in the shape of the trachea wall).

The connector 130 is configured to be detachably mounted on the proximal end 110 of the replacement ETT 100. The connector 130 is configured to enable connection of the replacement ETT 100 to a positioning arm capable of defining and securing the replacement ETT 100 at a user-defined insertion depth into the trachea 68. The connector 130 has a cross-sectional area (e.g., has a cross-sectional outer diameter) that is smaller than an inner cross-sectional area of the tube 100 in a fully expanded state or an inner cross-sectional area of a standard, non-expandable, ETT. For example, the connector 130 may have a circular end 132 with an outer diameter 134 of about 2 mm to about 5 mm smaller than the inner diameter 165.

Figure 2B:
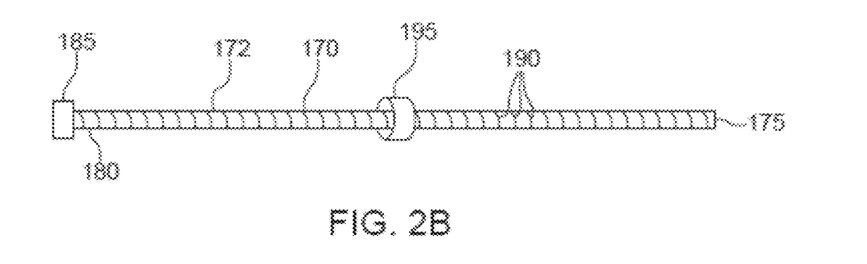
FIG. 2B is a side plan view of an ETT placement guide.

Referring also to FIG. 2B, an ETT placement guide 170 includes a rod 172, a detachable connector 185, and a depth lock 195. The rod 172 is an elongated member that may have any of a variety of cross-sectional shapes, e.g., circular, rectangular, a plus sign (+), a ring, etc. The rod 172 has a proximal end 175, a distal end 180, and scale markings 190. At least the scale markings 190 and the depth lock 195 are optional, and other placement guides may not include one or both of these features. The detachable connector 185 is configured to be detachably connected to the proximal end 110 of the replacement ETT 60. The detachable connector 185 may also be configured to be detachably connected to the distal end 180 of the guide 170. Also or alternatively, the connector 185 may be configured to connect to the connector 130.

The scale markings 190 may be configured to indicate depths to which the replacement ETT 100 is inserted into an endotracheal tube. As the replacement ETT 100 is inserted into another ETT, the scale markings 190 relay and confirm insertion depth of the replacement ETT 100 into the other ETT. The scale markings 190 may be configured to convey any of a variety of resolutions of depth, e.g., millimeters, centimeters, etc. The scale markings 190 may be within, part of, or on the surface of the rod 172. For example, the scale markings 190 may be etched or scribed into or onto the surface of the rod 172. Also or alternatively, the scale markings 190 may be printed on the rod 172. The scale markings 190 may be below an external surface of the rod 172, e.g., with the scale markings 190 coated by a suitable transparent material such that scale markings 190 are visible through the coating. As another example, the scale markings 190 may be inside the rod 172, with material of the rod 172 being sufficiently transparent to enable viewing of the scale markings 190. Also or alternatively, another mechanism may be provided as part of the placement guide 170 for indicating depth, such as a laser distance measurer and/or a digital read-out indicating the depth of the ETT 100. Still other techniques for determining and/or indicating depth of the ETT 100 may be used.

The depth lock 195 is configured to slide along the rod 172 and to be securely attached to the rod 172 at a user-defined position along a length of the rod 172. The depth lock 195, when secured to the rod 172, helps ensure that a replacement ETT such as the replacement ETT 100, attached to the placement guide 170 (e.g., by the connector 185), will not be inserted farther into a presently-inserted ETT (i.e., presently being used to ventilate a patient) than the user-defined depth. The depth lock 195 is configured to interfere with a proximal end of the presently-inserted ETT to inhibit further insertion of the replacement ETT into the presently-inserted ETT.

Figure 3:
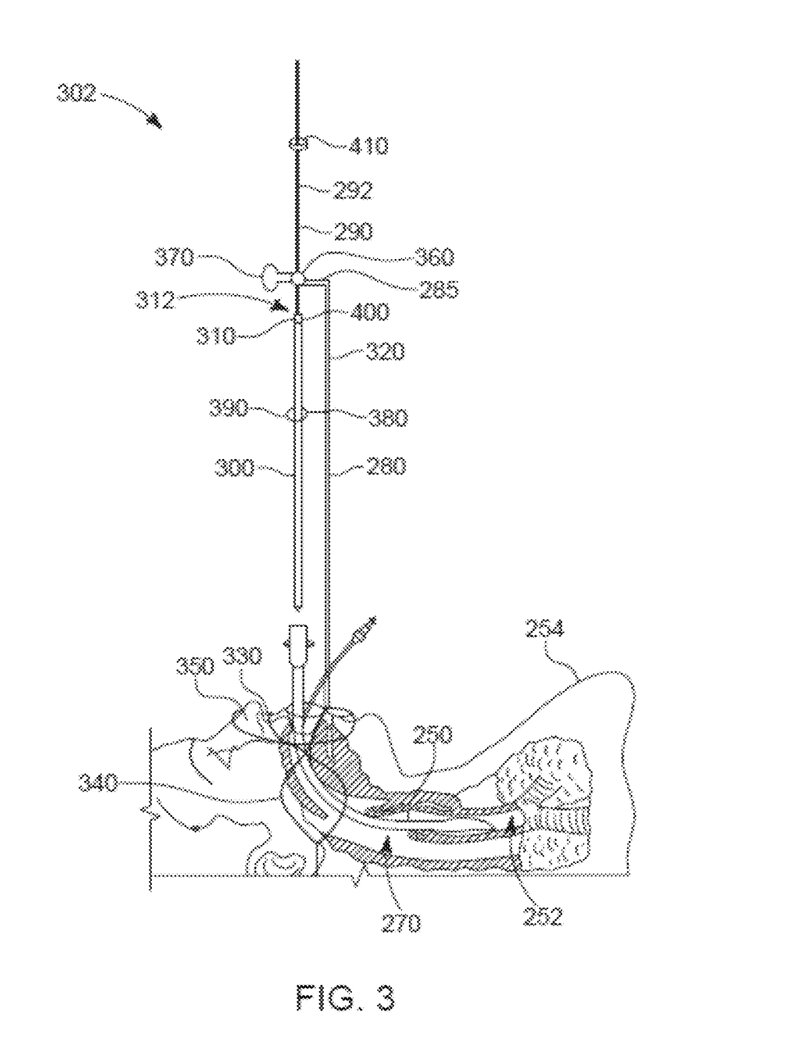
FIG. 3 is a partially-cross-sectional side plan view of a patient intubated with a previously placed or pre-existing ETT, and a side plan view of a re-intubation system.

Referring also to FIG. 3, a previously placed ETT 250 that is to be replaced is located at a desired insertion depth in the trachea 252 of a patient 254, and an ETT exchange system 302 that includes a replacement ETT 300 is positioned for insertion into the used ETT 250. The used ETT 250 is to be removed and discarded. A detachable connector 310 of a securement apparatus 280 is configured to connect to a distal end 312 of a placement guide 290 to secure the placement guide 290 to the replacement ETT 300 at a desired location. The replacement ETT 300 may be the replacement ETT 100 that is expandable across a cross-sectional area as discussed above. The securement apparatus 280 is an example, and other physical forms may be used including different quantities of vertical and horizontal members than shown. Further, the securement apparatus 280 may comprise a number of different materials used in various configurations and attachments to the patient's head.

The detachable connector 310 may be implemented using many different configurations that provide sufficient mechanical connection between the replacement ETT 300 and the guide 290 such that the replacement ETT 300 can be securely positioned and held within the used ETT 250, and allow detachment of the replacement ETT 300 from the guide 290. The connector 310 may be configured to be detachably connected to the replacement ETT 300 at a connection point of the replacement ETT 300 such that the connection point is fixed relative to a length of the guide 290, e.g., a rod 292. Thus, the position of the guide 290 will correspond to a position of the connection point, which may at a proximal end of the replacement ETT 300 or at a known distance from the proximal end of the replacement ETT 300. Alternatively, the connection point could move relative to a length of the guide 290. The connector 310 may be capable of repeated attachment and detachment, or may only be capable of a single detachment operation. An example of the connector 310 is a Luer lock connector. Another example of the connector 310 is a connector comprising a material that can be physically broken (e.g., by twisting). Other examples of the connector 310 include magnetic connectors or electromagnetic connectors. The detachable connector 310 may be configured to be detachably connected to an inner diameter of the replacement ETT 300. Also or alternatively, the connector 310 may be configured to be detachably connected to an outer diameter of the replacement ETT 300. Alternatively, the detachable connector may be connected to the proximal end of the replacement ETT. The detachable connector 310 may be a piece unto itself configured to interface between the guide 290 and the replacement ETT 300. Alternatively, the detachable connector 310 may be part of the guide 290 or part of the replacement ETT 300.

The securement apparatus 280 includes a vertical member 320 and a base 330, here a mouthpiece 330. The base 330 may be integral with the vertical member 320, or the vertical member 320 may be a separate piece that is attached to the base 330. The mouthpiece 330 is attached to a mouthpiece band 340 that is configured to secure the mouthpiece 330 to the patient 254 to help retain the position of the securement apparatus 280 relative to a throat 270 and the trachea 252 of the patient 254. The mouthpiece 330, in this example, includes a nose piece 350 that may help position the mouthpiece 330 relative to, and secure the mouthpiece 330 to, the patient 254. While in the example shown in FIG. 3, the mouthpiece 330 is used to position the securement apparatus 280 relative to the patient 254, other devices and/or methodologies may be used for this purpose. For example, the vertical member 320 could be attached to a frame surrounding a head of the patient 254. This frame may be fixed to the level of the maxilla or mandibular of the patient. For instance, if a patient has severe trauma to the mouth, instead of the mouthpiece 330, a system may be used that is secured to the patient's forehead (see forehead 50, FIG. 1), or secured to the sides of the patient's head, or secured to a table upon which the patient 254 lies. The securement apparatus may be fixed to the surface of the patient's table/OR bed.

Extending from the vertical member 320 is a horizontal member 285. The horizontal member 285 may be integral with the vertical member 320, or separate from, but attached to, the vertical member 320. The horizontal member defines a guide eyelet 360 at an end opposite to which the horizontal member 285 connects to the vertical member 320. The guide eyelet 360 is a hole sized to allow the rod 292 of the guide 290 to pass through the guide eyelet 360. Thus, the rod 292 is loosely coupled to the securement apparatus 280 (including the base of the securement apparatus), being movable (here slidable) relative to the securement apparatus 280. Other configurations for loosely coupling the rod 292 and the securement apparatus 280 may be used, e.g., a tongue and groove arrangement. The securement apparatus 280 further includes a guide lock mechanism configured to lock the rod 292 in place relative to the securement apparatus, e.g., the vertical member 320. Here, the guide lock mechanism is a set screw 370. The horizontal member 285 further defines a threaded hole configured to receive the set screw 370 such that turning the set screw 370 in the threaded hole tightens the set screw 370 against the rod 292 to secure the rod 292 between the set screw 370 and the horizontal member 320 at a user defined location, inhibiting the rod 292 from sliding within the guide eyelet 360. Though a screw is used to secure the rod 292 in this example, other securement means may be used. For example, securement means such as clamps, ratchets, wheels, detents, diameter restrictors, ridges, buttons, locking bars, an O-ring through which the rod 292 may be slid but that will hold the rod 292 in place absent a force pushing/pulling the rod 292 through the ring, etc.

The securement apparatus 280 includes supplemental horizontal member 380 that extends from the vertical member 320 and provides a supplemental guide eyelet 390. A supplemental set screw (not shown) may be used with the supplemental horizontal member 380 to provide supplemental securing of the rod 292 to the vertical member 320. The supplemental horizontal member 380 is optional. Further, more than the two horizontal members 285, 380 and corresponding set screws (or other securing means) shown may be used. Further, multiple vertical members can be used to improve the stability of the securement apparatus 280.

The guide 290 also includes a guide depth gauge 410. The guide depth gauge 410 is configured to slide along the rod 292 and to be fixed to the rod 292 at a desired location corresponding to a desired insertion depth of the replacement ETT 300. The guide depth gauge 410, when secured to the rod 292, helps ensure that the replacement ETT 300 will not be inserted farther into the used ETT 250 than the desired insertion depth. The rod 292 is configured (e.g., sized and shaped) to fit within an inner passageway of the replacement ETT 300 and the guide depth gauge 410 is configured not to be able to pass through the eyelet 360, i.e., is configured to interfere with the horizontal member 285 to inhibit further insertion of the replacement ETT 300 into the used ETT 250. Here, the guide depth gauge 410 has an inner radius greater than a radius of the guide eyelet 360 and smaller than a distance from the center of the guide eyelet 360 to the vertical member 320. The interference of the guide depth gauge 410 with the horizontal member 320, with the guide 290 attached to the replacement ETT 300 by a detachable connector 310 helps ensure that a user-selected position on the rod 292 does not pass the eyelet 360, thereby helping to ensure that the replacement ETT 300 does not exceed an acceptable insertion depth. Thus, the guide depth gauge 410 helps ensure that the replacement ETT 300 is not inserted into the used ETT 250 beyond a user specified insertion depth. That is, a user can establish a maximum endotracheal tube insertion depth, by using the guide depth gauge 410, before initiating the ETT exchange thereby offering a pro-active tool to help ensure that an endotracheal tube is not inserted beyond a medically-critical depth (e.g., to a depth where the ETT may touch the bifurcation 20).

Other configurations of guide depth gauges may be used. For example, a guide depth gauge may include a ring that slides over the rod 292 but that can be tightened against the rod 292 at a desired location or the rod 292 could have teeth that match a ratcheting system. The ring may be configured to be ratcheted down to a smaller inner diameter, to resist the diameter expanding, to secure the ring against the rod 292.

The guide 290 is detachably connected to the replacement ETT 300 via the detachable connector 310. Such detachable connections can come in a number of different forms and are commercially available from a number of different sources. For example, medical-grade Luer lock connectors may be used. Still other connectors, whether single de-connection or multiple connection and de-connection, may be used.

The replacement ETT 300 is configured to be inserted inside the used ETT 250 and to allow the used ETT 250 to be removed while the replacement ETT 300 stays inside the patient 254 at a user-defined insertion depth. For example, the replacement ETT 300 may be configured to slide within a passageway in the used ETT 250, e.g., within an inner diameter of a circular passageway of the used ETT 250. The replacement ETT 300 may be configured (e.g., sized, shaped, and of a material) such that the used ETT 250 may be slid over the replacement ETT 300 to remove the used ETT 250 from the patient 254.

The replacement ETT 300 is configured to conform to the wall of at least a portion of the trachea 252. For example, a cross-sectional area of at least a portion of the replacement ETT 300 may expand to contact the wall of the trachea 252. The replacement ETT 300 may form a seal with the wall of the trachea 252 to inhibit gas from the replacement ETT 300 from escaping the trachea 252 into a throat or mouth of the patient 254 and to facilitate effective ventilation of the patient 254. The replacement ETT 300 is configured such that a passageway inside the replacement ETT 300 is large enough to provide sufficient air flow for ventilating the patient 254. Although not shown in FIG. 3, the replacement ETT 300 may include a balloon cuff configured to be inflated. The balloon cuff is optional, and may be omitted, for example if a cross-sectional area of the replacement ETT 300 can sufficiently seal the trachea.

Further, a proximal end 400 of the replacement ETT 300 is configured to receive the detachable connector 310. The proximal end 400 may be configured to receive a ventilator connector, not shown. Various attachable ventilator connectors may be used such as ventilator connectors may by Mercury Medical, Mauser, Rusch, Mallinckrodt, and Medtronic.

The proximal end 400 of the replacement ETT 300 may also enable securement of the replacement ETT 300 to the patient 254 for prolonged intubation. For example, medical tape may be attached to the proximal end 400 and to the patient's skin to secure the replacement ETT 300 to the patient 254.

Figure 4:
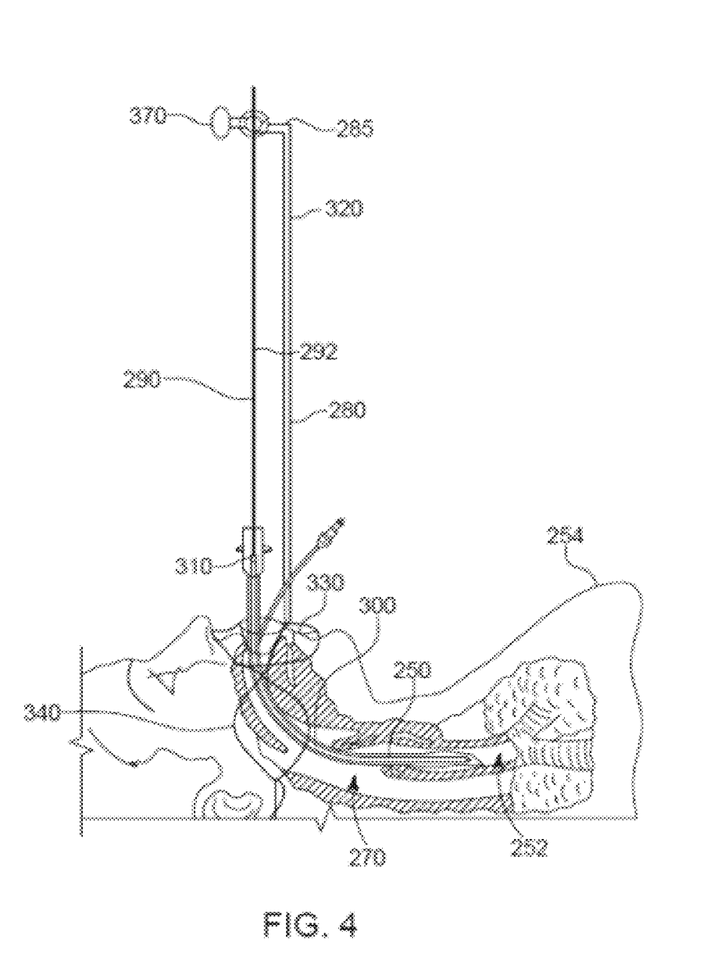
FIG. 4 is a partially-cross-sectional side plan view of the intubated patient shown in FIG. 3, with a replacement ETT of the re-intubation system shown in FIG. 3 inserted inside the previously placed or pre-existing ETT.

Referring also to FIG. 4, the used ETT 250 is located at the desired insertion depth of the trachea 252 of the patient 254, and the replacement ETT 300 is also positioned at the desired insertion depth into the trachea 252 of the patient 254. While the insertion depth of the used ETT 250 and the replacement ETT 300 are the same in this example, the replacement ETT 300 may be inserted to a different depth than the used ETT 250. During insertion of the replacement ETT 300, the inner passageway of the used ETT 250 guides the replacement ETT 300. That is, the replacement ETT 300 slides within the used ETT's inner passageway and the wall of the inner passageway directs the replacement ETT 300 into the patient's trachea 252. The guide 290 holds the replacement ETT 300 within the used ETT 250 at the desired insertion depth. The insertion depth of the replacement ETT 300 is fixed in a static state by use of the eyelet screw 370 as discussed above. As discussed above, the insertion depth is established according to the location of the guide depth gauge 410 on the rod 292 to help ensure that the replacement ETT 300 is not inserted farther into the trachea 252 than desired, and is inserted into the trachea 252 at least as far as desired.

Figure 5:
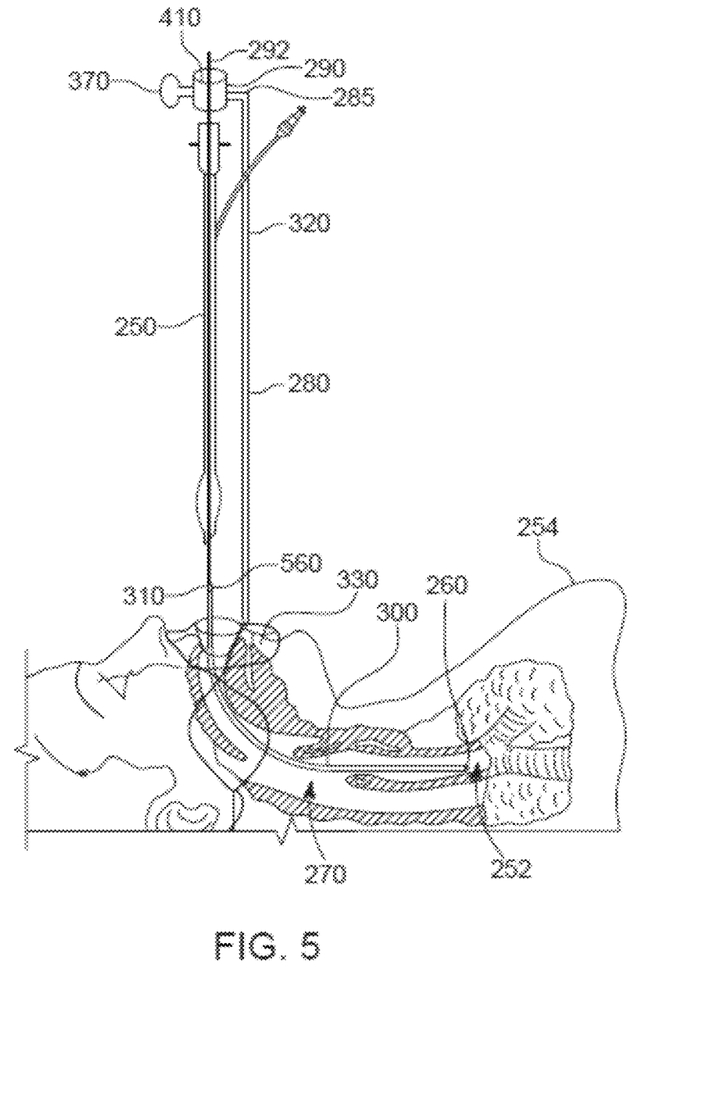
FIG. 5 is a partially-cross-sectional side plan view of the intubated patient shown in FIG. 4, with the replacement ETT of the re-intubation system shown in FIG. 3 inserted inside the patient and the previously placed or pre-existing ETT extracted from the patient.

Referring also to FIG. 5, the used ETT 250 has been removed from the patient 254, and a distal end 260 of the replacement ETT 300 remains positioned at the desired insertion depth into the trachea 252 of the patient 254. The replacement ETT 300 is secured at the depth of insertion by use of the guide eyelet screw 370 as previously described. The guide eyelet screw 370 secures the rod 292 to the horizontal member 285, and the detachable connector 310 attaches the rod 292 to the replacement ETT 300. In this way, the replacement ETT 300 may be fixed in position in the patient 254. As shown, the rod 292 and the securement apparatus 280 are long enough such that the used ETT 250 can be completely removed from the patient 254, and be disposed between the detachable connector 310 and the horizontal member 285. To remove the used ETT 250, a cross-sectional area of the used ETT 250 may be reduced (e.g., an inflated cuff deflated before removal of the used ETT). The used ETT 250 is removed by sliding the used ETT 250 over the replacement ETT 300 out of the patient 254 and beyond the detachable connector 310. The replacement ETT 300 and the rod 292 act as guides for the extraction or removal of the used ETT 250, while maintaining the predefined position of the replacement ETT 300 within the trachea 252.

Figure 6:
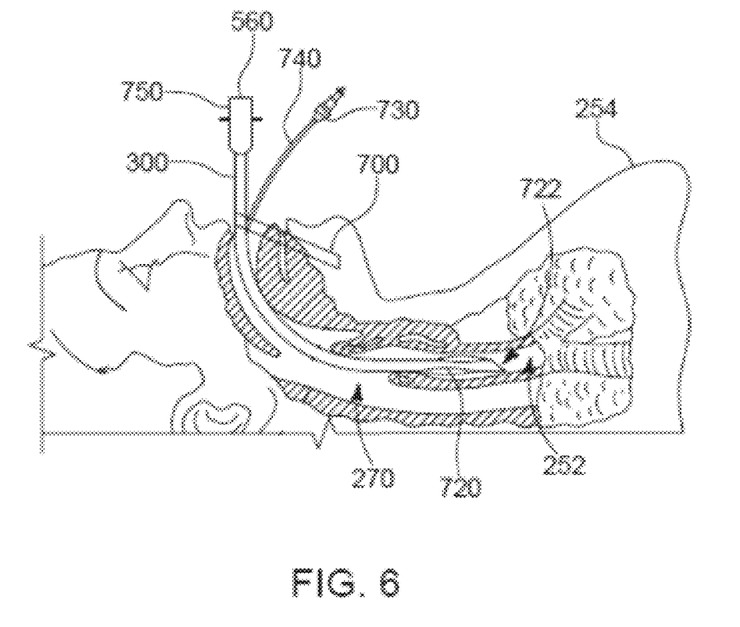
FIG. 6 is a partially-cross-sectional side plan view of the intubated patient with the replacement ETT inserted inside the patient, and with the previously placed or pre-existing ETT and the re-intubation system shown in FIG. 3 having been removed.

Once the used ETT 250 has been moved beyond the detachable connection 310, the used ETT 250, the rod 292, and the securement apparatus 280 can be removed. The detachable connector 310 can be actuated to disconnect the rod 292 from the replacement ETT 300. The securement apparatus 280 can be disconnected from the patient 254. The used ETT 250, the rod 292, and/or the securement apparatus 280 may be cleaned (e.g., sterilized) for re-use or disposed. The rod 292 may be disconnected from the replacement ETT 300 before securing the replacement ETT 300 to the patient (e.g., using surgical tape) as friction between the replacement ETT 300 (especially once expanded) and the patient will likely hold the replacement ETT 300 in place sufficiently while the rod 292 is detached from the replacement ETT 300. Alternatively, the replacement ETT 300 may be secured to the patient 254 before disconnecting the rod 292 from the replacement ETT 300. As shown in FIG. 6, the replacement ETT 300 can be secured to the patient 254 by standard means, e.g., tape 700, special mouth pieces with a clamp to hold the replacement ETT, silk or other cloth tape, etc. The replacement ETT 300 can have a cross-sectional-area expanded as discussed above. An expansion impetus (e.g., compressed air, mechanical means, springs, removal of sheaths that restrict expansion until removed, or other means) to enable/induce expansion of the replacement ETT may be used depending upon the configuration of the replacement ETT.

The replacement ETT 300 may include a balloon cuff 720 near or at a distal end 722 of the replacement ETT 300. The balloon cuff is optional and may be omitted, e.g., if the replacement ETT 300 can expand to seal the trachea 252 (e.g., contact the tracheal mucosa around a perimeter of the replacement ETT 300) sufficiently to enable adequate ventilation. If the balloon cuff 720 is present, the balloon cuff 720 may be inflated to seal the trachea 252. The replacement ETT 300 may include a pilot balloon 730 to inflate the balloon cuff 720. The pilot balloon 730 may be attached to a balloon cuff feed line 740 to inflate the balloon cuff 720. If the balloon cuff 720 is omitted, then the pilot balloon 730 and the balloon cuff feed line 740 may be omitted as well.

A ventilator connector 750 is attached to a proximal end 560 of the replacement ETT 300 and is configured to be connected to a ventilator (not shown) or a manual ventilation device.

Figure 7:
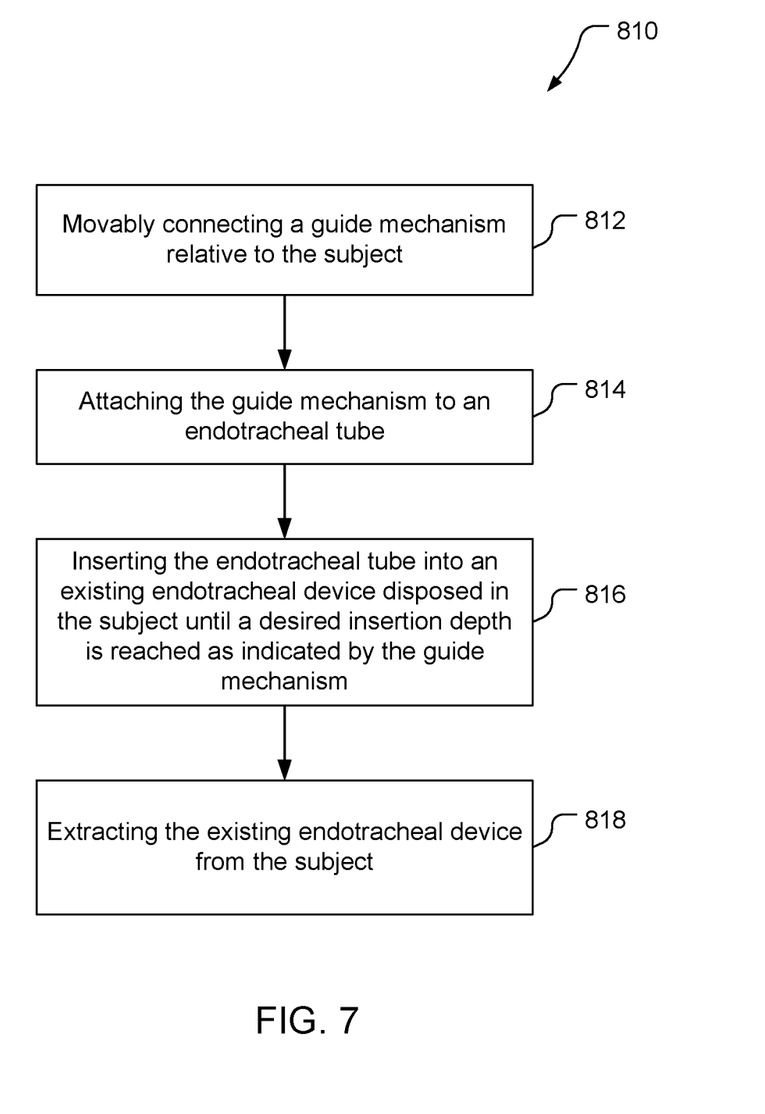
FIG. 7 is a block flow diagram of a method of intubating a subject.

Referring to FIG. 7, with further reference to FIGS. 1-6, and particular reference to FIG. 3, a method 810 of intubating a subject includes the stages shown. The method 810 is, however, an example only and not limiting. The method 810 may be altered, e.g., by having stages added, removed, rearranged, combined, performed concurrently, and/or having single stages split into multiple stages.

At stage 812, the method 380 includes movably connecting a guide mechanism relative to the subject. For example, the guide 290 may be slidably connected to the securement apparatus 280, e.g., by attaching the base 330 to the patient 254 using the band 354, and sliding the guide 290 into the guide eyelet 360 of the horizontal member 285 which is attached to the base 330 by the vertical member 320. Numerous other techniques for movably connecting a guide mechanism to a subject may be used.

At stage 814, the method 810 includes attaching the guide mechanism to an endotracheal tube. For example, the guide 290 may be connected to the ETT 300 using the connector 310 using any available technique based on the type of the connector 310.

At stage 816, the method 810 includes inserting the endotracheal tube into an existing endotracheal device disposed in the subject until a desired insertion depth is reached as indicated by the guide mechanism. For example, the ETT 300 may be inserted into an endotracheal device such as the ETT 250 disposed in the throat 270 of the patient 254, which may help inhibit injury to the patient 254 by avoiding contact between the ETT 300 and the patient 254 during insertion of the ETT 300. The ETT 300 may be inserted into the ETT 250 until a desired depth as indicated by the guide depth gauge 410, which may help inhibit injury to the patient 254 due to over-insertion of the ETT 300.

At stage 818, the method 810 includes extracting the existing endotracheal device from the subject. For example, the guide eyelet screw 370 may be tightened to secure the rod 292 to the horizontal member 285 to hold the ETT 300 in a fixed position relative to the patient 254. The used ETT 250 (or other endotracheal device) may be pulled from the patient 254 over the connector 310 with the ETT 300 and the rod 292 guiding the extraction.

The method 810 may include one or more further features. The method 810 may include setting the desired insertion depth on the guide mechanism before inserting the endotracheal tube into the subject. For example, the guide depth gauge 410 may be slid along the rod 292 and fixed to the rod 292 at a desired location corresponding to the desired depth of the ETT 300 to be inserted. The method 810 may include detaching the guide mechanism from the endotracheal tube after extracting the existing endotracheal device from the subject. For example, the connector 310 may be actuated to disconnect the rod 292 from the ETT 300, e.g., after extraction of the ETT 250 (or other endotracheal device) from the patient 254, and the used ETT 250 handled as desired, e.g., discarded, cleaned for re-use, etc. The method 810 may include expanding a cross-sectional area of the endotracheal tube to seal the endotracheal tube against a wall of a trachea of the subject after extracting the existing endotracheal device from the subject. For example, the cuff 140 may be inflated to seal the ETT 300 against the wall of the trachea of the patient 254. Attaching the guide mechanism to the endotracheal tube in the method 810 may comprise attaching the guide mechanism to the endotracheal tube at a connection point of the endotracheal tube such that the connection point is fixed relative to a length of the guide mechanism. For example, the connector 310 may be fixed to an end of the ETT 300 and attached to the end of the rod 292 so that the connector 310, and thus the ETT 300, is fixed relative to the length of the guide 290 such that the position of the guide 290 corresponds to a position of the ETT 300 relative to the patient 254 (e.g., depth in the throat 270 of the patient 254).

One or more further actions may be taken in addition to (either before or after) the method 810. For example, the ETT 300 may connected to a ventilator, e.g., after placement in the patient 254, and the ventilator operated to ventilate the patient through the ETT 300.

Other Considerations

Other examples and implementations are within the scope and spirit of the disclosure and appended claims. Substantial variations may be made in accordance with specific requirements.

As used herein, "or" as used in a list of items prefaced by "at least one of" or prefaced by "one or more of" indicates a disjunctive list such that, for example, a list of "at least one of A, B, or C," or a list of "one or more of A, B, or C," or "A, B, or C, or a combination thereof" means A or B or C or AB or AC or BC or ABC (i.e., A and B and C), or combinations with more than one feature (e.g., AA, AAB, ABBC, etc.).

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. This description provides example configurations only, and does not limit the scope, applicability, or configurations of the claims. Rather, the preceding description of the configurations provides a description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of operations may be undertaken before, during, or after the above elements are considered. Accordingly, the above description does not bound the scope of the claims.

What is claimed is:

1. An intubation system comprising:
   a base configured to be secured relative to a subject;
   a guide movably coupled to the base to allow the guide to move relative to the base;
   a securement apparatus connected to and extending away from the base for coupling the guide to the base; and
   a connector configured to be connected to a distal end of the guide and to detachably connect to a first endotracheal tube such that as the guide is moved relative to the base toward the subject, the first endotracheal tube is inserted into the subject;
   wherein the guide is sized and shaped to have a second endotracheal tube removed from the subject and slid over the guide while the securement apparatus secures the first endotracheal tube in the subject such that control of an airway of the subject is maintained while exchanging the first endotracheal tube for the second endotracheal tube in the airway of the subject.

2. The system of claim 1, wherein the guide comprises a rod and a guide lock mechanism configured to lock the rod in place relative to the base.

3. The system of claim 1, wherein the guide comprises a depth gauge.

4. The system of claim 3, wherein the depth gauge is indicative of a position of the endotracheal tube relative to the base.

5. The system of claim 4, wherein the guide comprises a depth lock mechanism configured to inhibit movement of the guide past a location corresponding to the depth lock mechanism to inhibit insertion of the endotracheal tube beyond a threshold depth in the subject.

6. The system of claim 5, wherein the base comprises a mouthpiece having a shape approximating a shape of a face of the subject adjacent a mouth of the subject.

7. The system of claim 1, further comprising the first endotracheal tube, wherein the first endotracheal tube is an expandable endotracheal tube configured such that at least a portion of a length of the first endotracheal tube has an expandable cross-section.

8. An intubation system comprising:
   means for guiding an endotracheal tube into an existing endotracheal device in a subject and for guiding the existing endotracheal device while the existing endotracheal device is extracted from the subject;
   means for holding the endotracheal tube in place relative to the subject while the existing endotracheal device is extracted from the subject such that control of an airway of the subject is maintained while exchanging the existing endotracheal device for the endotracheal tube in the airway of the subject; and
   means for releasing the endotracheal tube.

9. The system of claim 8, further comprising means for indicating a depth of the endotracheal tube in the subject.

10. The system of claim 8, further comprising means for inhibiting insertion of the endotracheal tube beyond a desired depth in the subject.

11. The system of claim 8, wherein the means for guiding comprise means for movably connecting the means for guiding relative to the subject.

12. A method of intubating a subject, the method comprising:
    movably connecting a guide mechanism relative to the subject;
    attaching the guide mechanism to an endotracheal tube;
    inserting the endotracheal tube into an existing endotracheal device disposed in the subject until a desired insertion depth is reached as indicated by the guide mechanism and while maintaining control of an airway of the subject; and
    extracting the existing endotracheal device from the subject by sliding the existing endotracheal device over the guide mechanism while maintaining control of the airway of the subject by leaving the endotracheal tube in the subject.

13. The method of claim 12, further comprising setting the desired insertion depth on the guide mechanism before inserting the endotracheal tube into the subject.

14. The method of claim 12, further comprising detaching the guide mechanism from the endotracheal tube after extracting the existing endotracheal device from the subject.

15. The method of claim 12, further comprising expanding a cross-sectional area of the endotracheal tube to seal the endotracheal tube against a wall of a trachea of the subject after extracting the existing endotracheal device from the subject.

16. The method of claim 12, wherein attaching the guide mechanism to the endotracheal tube comprises attaching the guide mechanism to the endotracheal tube at a connection point of the endotracheal tube such that the connection point is fixed relative to a length of the guide mechanism.

\* \* \* \* \*